United States Patent [19]

Tawara et al.

[11] Patent Number: 4,958,283
[45] Date of Patent: Sep. 18, 1990

[54] METHOD AND SYSTEM FOR STORING AND COMMUNICATING MEDICAL IMAGE DATA

[75] Inventors: Kiyoshi Tawara; Takehiro Ema; Eitaro Nishihara, all of Ootawara, Japan

[73] Assignee: Kabushiki Kaisha Toshiba, Kawasaki, Japan

[21] Appl. No.: 216,338

[22] Filed: Jul. 8, 1988

[30] Foreign Application Priority Data

Jul. 8, 1987 [JP] Japan ................ 62-170308
Jul. 8, 1987 [JP] Japan ................ 62-170310
Jul. 8, 1987 [JP] Japan ................ 62-170311

[51] Int. Cl.$^5$ .................................. G06F 15/42
[52] U.S. Cl. ..................... 364/413.13; 350/96.16; 364/134; 364/240.6; 364/200; 364/242.94
[58] Field of Search ............... 350/96.16; 364/134, 364/133, 131, 413.13, 200 MS; 370/85, 88, 85.9

[56] References Cited

U.S. PATENT DOCUMENTS

4,653,112 3/1987 Ouimette ................ 364/513 X
4,672,683 6/1987 Matsueda ................ 382/57
4,688,168 8/1987 Gudaitis et al. ......... 364/134 X
4,775,210 10/1988 Fioretti ................. 350/96.16
4,781,427 11/1988 Husbands et al. ......... 350/96.16
4,817,050 3/1989 Komatsu et al. ......... 364/900
4,817,177 3/1989 Shimizu ................. 350/96.16 X
4,826,275 5/1989 Heinzman ............... 350/96.16

Primary Examiner—Jerry Smith
Assistant Examiner—Steven G. Kibby
Attorney, Agent, or Firm—Oblong, Spivak, McClelland, Maier & Neustadt

[57] ABSTRACT

When medical image data is acquired by imaging equipment of modality, modality outputs an image data transfer request command to a data base, via a network. After a memory area of a TMD (temporal magnetic disc) of the data base is secured, the acquired image data is transferred from modality to the TMD. When an image data retrieval request command is input from a WS (work station) of a console to data base through network, retrieval of the image data stored in the data base is performed, the retrieved data is transferred to the WS, and is displayed. The operator requests data base to read out image data by retrieval result. Data base is searched memory address of the requested image data. When the requested image data is stored in OD (optical disc), image data stored in OD is transferred to TMD. Image data stored in TMD is transferred to WS, and is displayed.

6 Claims, 13 Drawing Sheets

METHOD AND SYSTEM FOR STORING AND COMMUNICATING MEDICAL IMAGE DATA

BACKGROUND OF THE INVENTION

1. Field of the Invention

The present invention relates to a method and system for storing a large amount of medical image data acquired by various medical image data acquiring apparatuses, such as an X-ray photographing apparatus, an X-ray CT (computed tomography) apparatus and an ultrasound diagnosis apparatus, and communicating medical image data.

2. Description of the Related Art

Conventionally, medical image data, after being acquired by various medical image data acquiring apparatuses, is stored in a data base, and in the case of performing diagnosis medical image data is accessed.

With a conventional system, however, the medical image data is not stored in a data base separately for each of departments, such as the internal medical department, the surgery department and the department of obstetrics or for each of various kinds of medical images, such as the X-ray image, the X-ray CT image and the ultrasound image. As a result, in order to retrieve an X-ray CT image of a patient, for example, all the image data stored in the data base must be retrieved, which is a time-consuming process. In addition, if the data base is accessed simultaneously by a number of departments, this further increases the time required to retrieve the desired image data.

For this reason, a system is desired which efficiently performs the retrieval and communication process of the medical image data stored in the data base.

SUMMARY OF THE INVENTION

It is an object of this invention to provide a method and system for storing a large amount of medical image data acquired by various medical image data acquiring apparatuses, and communicating medical image data.

According to one aspect of the present invention, there is provided a system for storing and communicating medical image data, the system comprising:

image data acquiring means for acquiring medical image data;

image data storing means for storing the medical image data acquired by the image data acquiring means;

image data accessing means for accessing the medical image data stored in the image data storing means;

first network means for communicating the medical image data by connecting the image data acquiring means and the image data storing means; and second network means for communicating the medical image data by connecting the image data storing means and the image data accessing means.

According to another aspect of the present invention, there is provided a method for storing and communicating medical image data, the method comprising the steps of:

(a) acquiring the medical image data;

(b) communicating the medical image data acquired in step (a), after an image data transfer command is transmitted;

(c) storing the medical image data communicated in step (b), after the image data transfer command is received;

(d) accessing the medical image data stored in step (c), after image data request command is transmitted;

(e) communicating the medical image data accessed in step (d), after the image data request command is received; and (f) displaying the medical image data communicated in step (e).

DETAILED DESCRIPTION OF THE PREFERRED EMBODIMENTS

The above-mentioned embodiments of this invention will hereinafter be described, with reference to the drawings.

Figure 1:
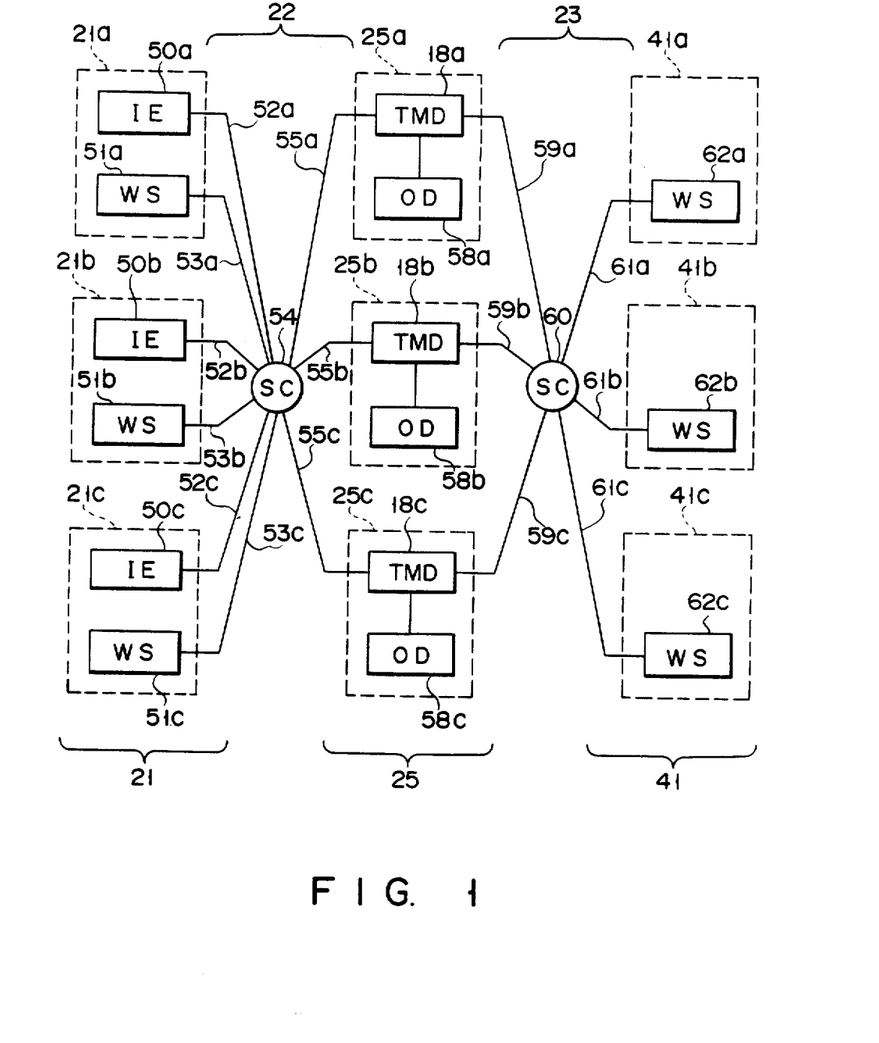
FIG. 1 is a block diagram of a medical image data storage and/communication system according to a first embodiment of this invention.

The medical image data storage and communication system shown in FIG. 1 essentially comprises modality 21, data base 25 and console 41. Data base 25 is connected to modality 21 by network 22, and to console 41 by network 23. More specifically, modality 21 includes, for example, modality 21a such as an X-ray photographing apparatus, modality 21b such as an X-ray CT apparatus and modality 21c such as an ultrasonic diagnosis apparatus which are installed in an examination room of a hospital. Data base 25 includes, for example, an internal medical department data base 25a for storing image data used in the internal medical department, surgery-department data base 25b for storing image data used in the surgery department, and obstetrics-department data base 25c for storing image data used in the department of obstetrics. Console 41 includes, for example, internal medical department console 41a, surgery department console 41b, and obstetrics department console 41c which are installed in consultation rooms for outpatients to access image data stored in data base 25. Data base 25 stores a large quantity of image data in accordance with classified items, e.g., for each of the departments such as the internal department, the surgery department, and the obstetrics department. Console 41 reads out image data from data base 25.

Modalities 21a, 21b, 21c comprise imaging equipments (IEs) 50a, 50b, 50c used for acquiring various image data for specified parts of subjects under examination, and work stations (WSs) 51a, 51b, 51c used for displaying and processing the image data acquired by IEs 50a, 50b, 50c. Data bases 25a, 25b, 25c comprise temporal magnetic discs (TMDs) 18a, 18b, 18c for storing image data temporarily, and optical discs (ODs) 58a, 58b, 58c for storing image data for a long time. TMDs 18a, 18b, 18c have a smaller memory capacity, but a higher data transfer rate than ODs 58a, 58b, 58c. Consoles 41a, 41b, 41c comprise WSs 62a, 62b, 62c used for accessing and displaying image data stored in data base 25. WSs 51a, 51b, 51c and WSs 62a, 62b, 62c each comprise a keyboard, a display, a microprocessor, etc., which are not shown, and are used for accessing image data.

Network 22 comprises star coupler (SC) 54, lines 52a, 52b, 52c connecting SC 54 to IEs 50a, 50b, 50c, lines 53a, 53b, 53c connecting SC 54 to WSs 51a, 51b, 51c, and lines 55a, 55b, 55c connecting SC 54 to TMDs 18a, 18b, 18c. Network 23 comprises SC 60, lines 59a, 59b, 59c connecting SC 54 to TMDs 18a, 18b, 18c, and lines 61a, 61b, 61c connecting SC 60 to WSs 62a, 62b, 62c. Each of these lines can be constituted by an optical fiber cable. SC 54 and SC 60 have a function of outputting to plural directions data incoming from a direction. Networks 22 and 23 are managed by a network controller (not shown).

The operation of the image data storage and communication system constituted as above will now be described.

When image data is acquired by, for example, IE 50a of modality 21a modality 21a outputs a request command via network 22, for transferring of the image data to data base 25. In data base 25, after memory areas of TMDs 18a to 18c are secured, the image data is transferred from IE 50a to TMDs 18a to 18c.

On the other hand, when, for example, a retrieval request command for retrieving image data is output from WS 62a of console 41a to data base 25 via network 23, the retrieval of the stored image data is performed in data base 25. The retrieval result is transferred to WS 62a for displaying on the display. A doctor requests data base 25 to read out image data in accordance with the displayed retrieval result. The stored area of the requested image data is examined in data base 25. When the requested image data is stored in one of ODs 58a to 58c, it is transferred to one of TMDs 18a to 18c and then transferred to WS 62a. The transferred image data is visually displayed in WS 62a.

Figure 2:
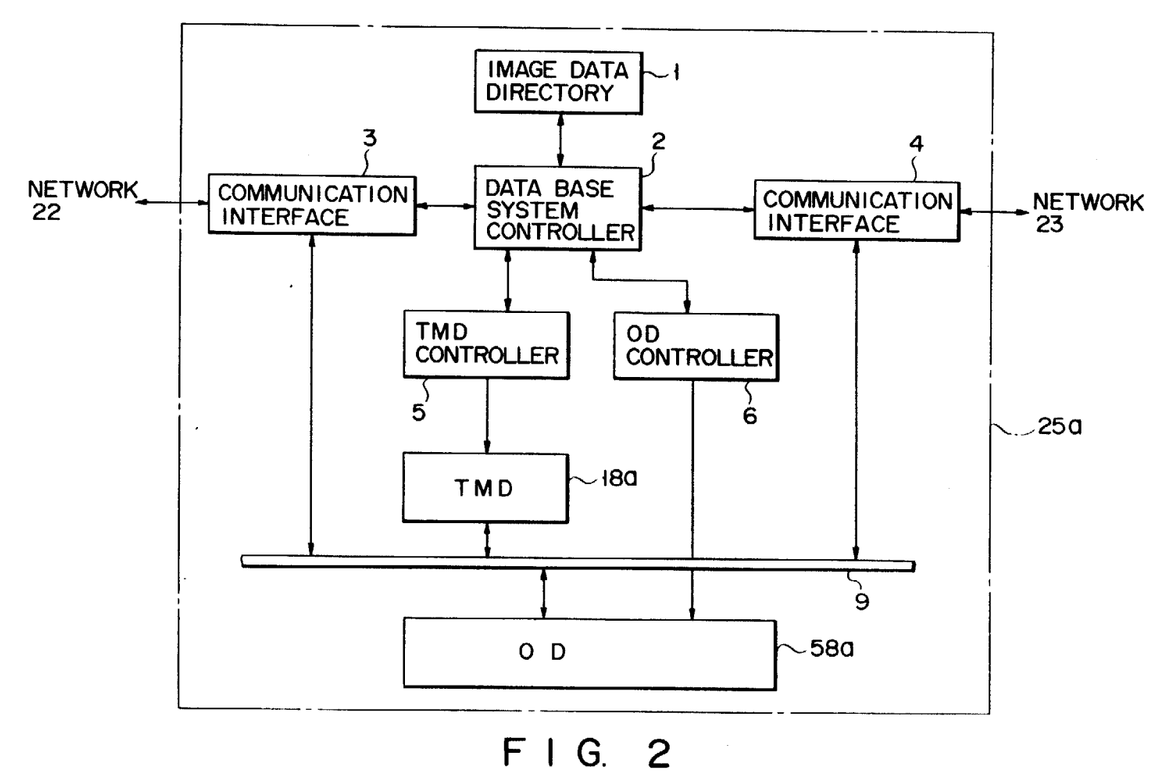
FIG. 2 is a block diagram of the data base shown in FIG. 1.
Figure 3A:
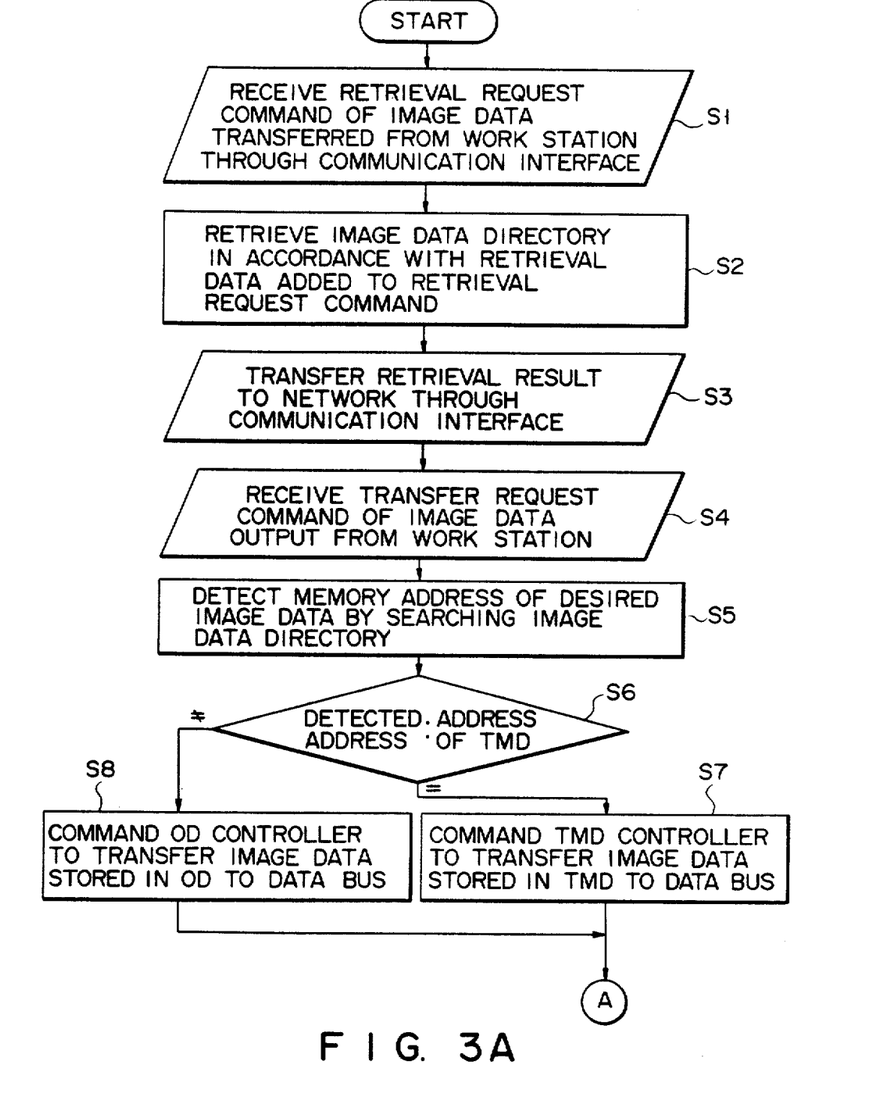
FIGS. 3A and 3B are flowcharts for explaining the operation of the data base shown in FIG. 2.
Figure 3B:
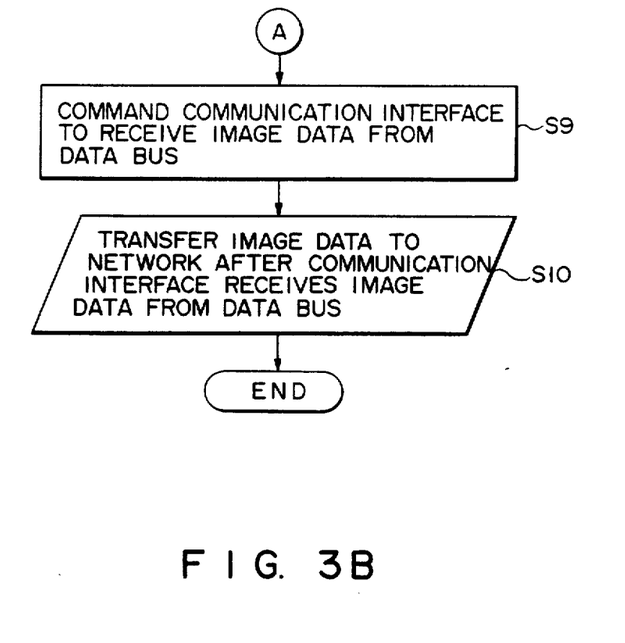

The operation of data base 25a will now be described in detail, with reference to FIGS. 2, 3A, and 3B.

In step S1, a retrieval request command transferred from a predetermined work station is received by data base system controller 2 through communication interface 3 or 4. In step S2, image data directory 1 is searched in accordance with the retrieval data added to the retrieval request command. The retrieval data includes, for example, the patient identification (ID), the examination date, the modality name. A retrieval table for image data stored in TMD 18a and OD 58a has been prepared in image data directory 1 in advance. In step S3, the retrieval result obtained in step S2 is transferred through communication interface 3 (or 4) and network 22 (or 23) to a predetermined work station at which it will be displayed.

A transfer request command is input by the predetermined work station including the keyboard or other input device and is transferred to network. In step S4, the transfer request command output from the predetermined work station is received by data base system controller 2 through communication interface 3 (or 4). The transfer request command includes data for specifying the image data acquired by modality 21. In step S5, the memory address of the image data to be transferred is detected by searching image data directory 1.

In step S6, the store location of image data is judged on the basis of the memory address detected in step S5. In step S6, if the image data is stored in TMD 18a, then data base system controller 2 commands TMD controller 5 to output the image data corresponding to the detected memory address on data bus 9 (step S7). In step S6, if the image data is stored in OD 58a, then data base system controller 2 commands OD controller 6 to output the image data corresponding to the detected memory address to data bus 9 (step S8).

In step S9, data base system controller 2 commands communication interface 3 or 4 to receive the image data output on data bus 9. In step S10, after the image data is received from data bus 9, communication interface 3 or 4 receives data representing the destination output from data base system controller 2 to transfer the image data to network 22 or 23.

By the above operations the transfer of image data is carried out.

In this case, however, because the image data transferred from modalities 21a to 21c and the image data to be transferred to consoles 41a to 41c must be stored in TMD 18a, it is necessary for TMD controller 5 to logically differentiate between them.

Figure 4:
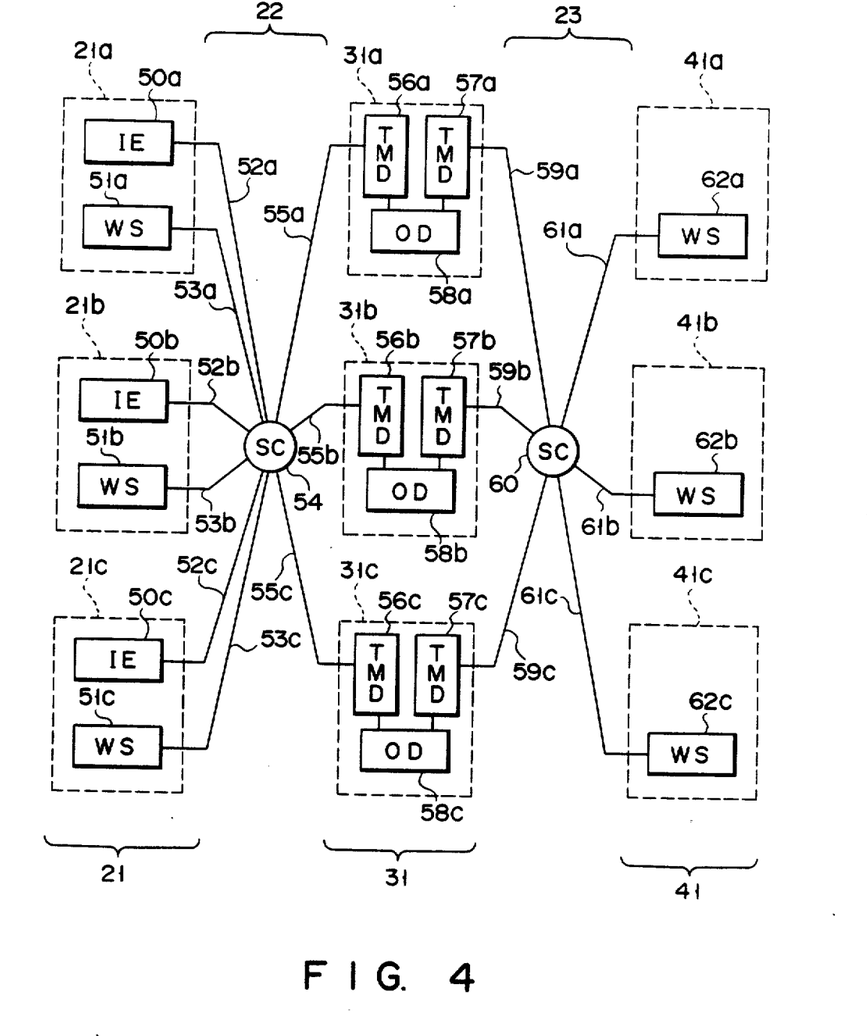
FIG. 4 is a block diagram of a medical image data storage and communication system according to a second embodiment of this invention.

As can been seen in FIG. 4, the second system comprises modality 21, data base 31, console 41, and networks 22 and 23, and is the same in arrangement as the first system except data base 31.

Data bases 31a to 31c comprise first TMDs 56a to 56c and second TMDs 57a to 57c. First TMDs 56a to 56c are coupled to IEs 50a to 50c via lines 55a to 55c, SC 54 and lines 52a to 52c of network 22. Second TMDs 57a to 57c are coupled to WSs 62a to 62c via lines 59a to 59c, SC 60 and lines 61a to 61c of network 23. First TMDs 56a to 56c and second TMDs 57a to 57c are coupled to 20 to ODs 58a to 58c, respectively. First TMDs 56a to 56c and second TMDs 57a to 57c are each arranged to store image data temporarily, and image data stored in TMDs 56a to 56c is transferred to ODs 58a to 58c when a predetermined amount of image data is stored or a predetermined command is input from predetermined work station.

Figure 5:
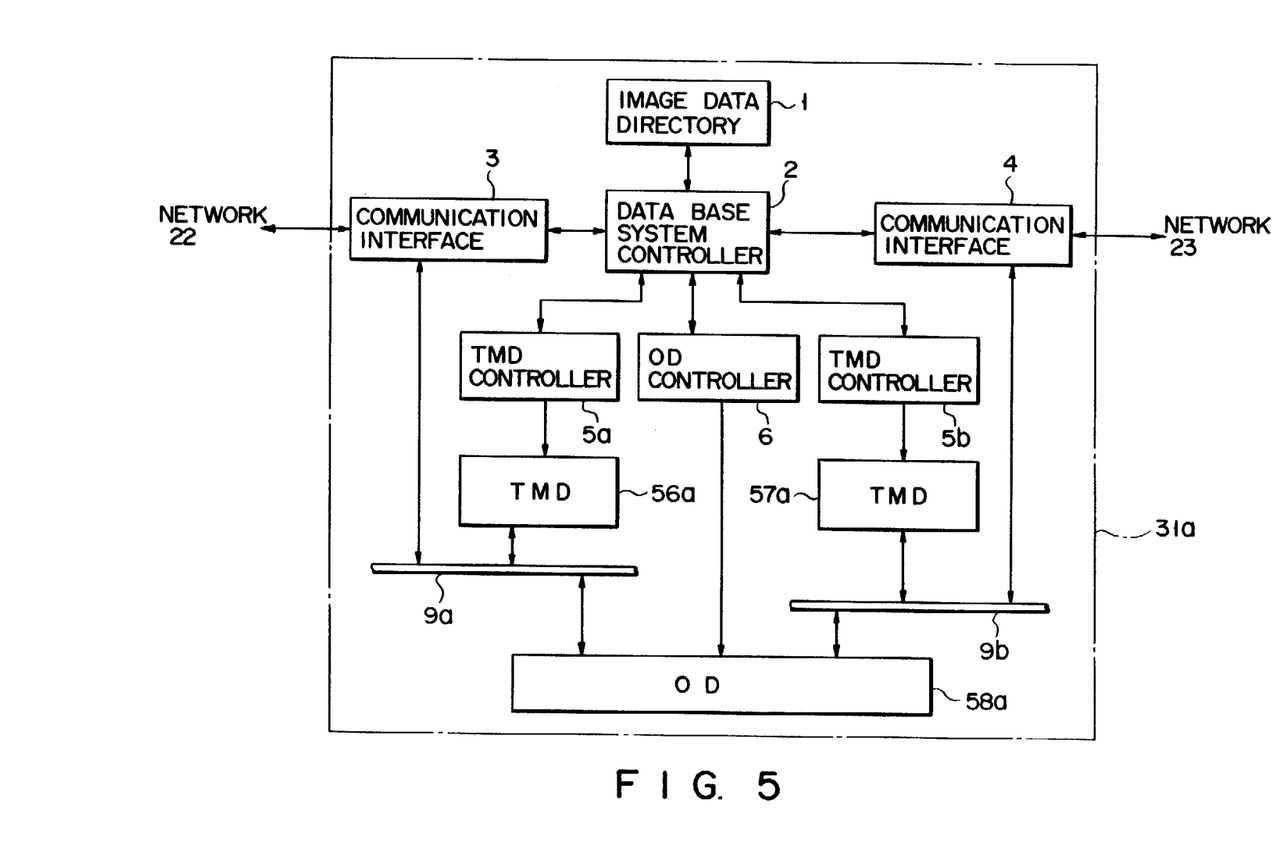
FIG. 5 is a block diagram of the data base shown in FIG. 4.

Next, the operation of the second system will be described. It is to be noted that the basic operation of data base 31a shown in FIG. 5 is the same as that of data base 25a of the first system.

It is assumed that image data is stored in OD 58a of data base 31a, and data base system controller 2 receives through communication interfaces 3 and 4 transfer request commands simultaneously output from WS 51a of modality 21a and WS 62a of console 41a to data base 31a. Data base system controller 2 controls OD controller 6 by the request from WS 51a so that the image data is transferred from OD 58a to first TMD 56a. The image data transferred to first TMD 56a is transferred to WS 51a via communication interface 3, line 55a, SC 54 and line 53a. On the other hand, data base system controller 2 also controls OD controller 6 by the request from WS 62a to transfer the image data from OD 58a to second TMD 57a. The image data thus transferred to second TMD 57a is transferred to WS 62a via communication interface 4, line 59a, SC 60 and line 61a. Namely, four operations are performed:

(1) the image data is transferred from OD 58a to first TMD 56a;

(2) the image data is transferred from OD 58a to second TMD 57a;

(3) the image data is transferred from first TMD 56a to WS 51a; and (4) the image data is transferred from second TMD 57a to WS 62a.

For these operations, operations (1) and (4); operation (2) and (3); and operations (3) and (4) may be performed in parallel, but operations (1) and (2) cannot be performed in parallel.

After the image data is transferred from OD 58a to TMD 56a, 57a, the image data is transferred from TMD 56a, 57a to WS 51a, 62a via network 22, 23, because the transfer rate of TMDs 56a and 57a is high as compared with that of OD 58a as described above, time period for occupying network is short, and the efficiency is high.

As described above, TMD controllers 5a, 5b can independently operate in response to request command transferred from networks 22, 23 connected to TMDs 56a, 57a.

By way of example, in the outpatients' department of a hospital, when image data is displayed in the order of accepted outpatients, outpatient acceptance data (outpatient ID, acceptance order etc ...) is transferred from a predetermined work station to the data base system controller. The data base system controller retrieves the image data of the outpatient on the basis of the acceptance data output from the predetermined work station. When the image data of the outpatient is stored in the OD of the data base, the data base system controller commands the OD controller to transfer the image data stored in the OD to the TMD. Next, when a transfer request command is output from the predetermined work station to the data base, the data base system controller commands the TMD controller to transfer the image data of the outpatient stored in the TMD to the predetermined work station. Thus, by processing image data of patients in advance, it is possible to improve the efficiency of image data transfer.

Figure 6:
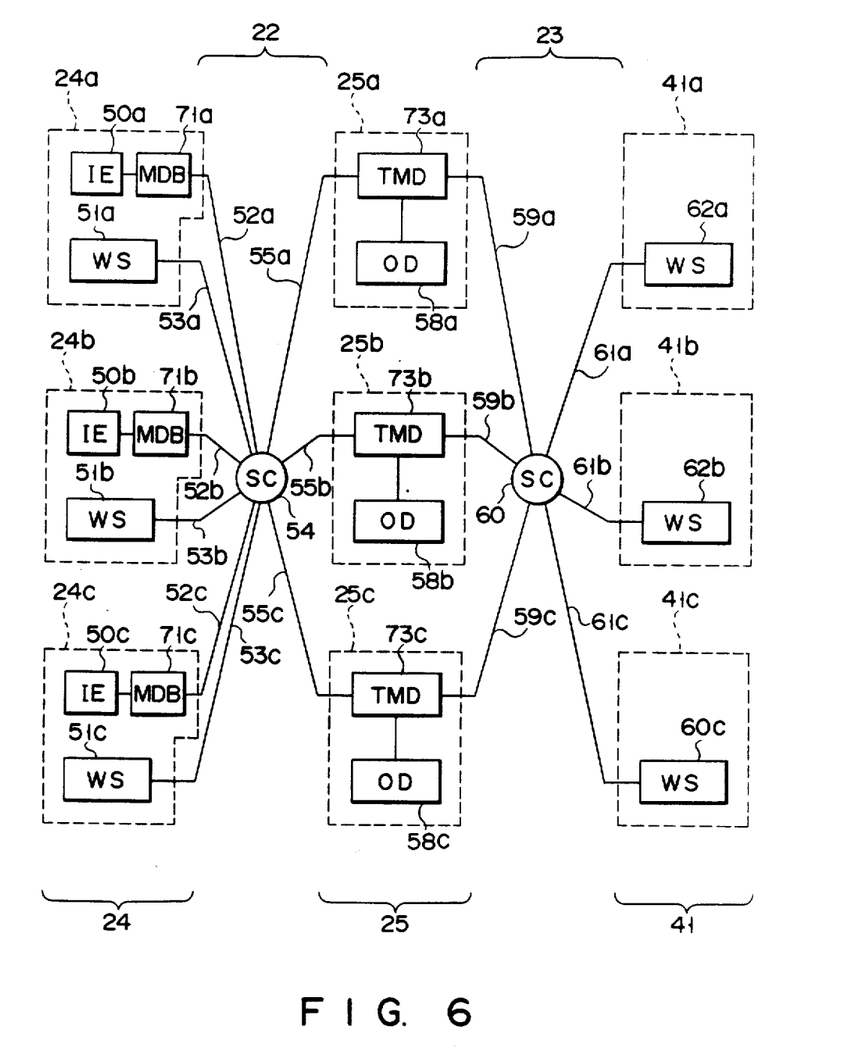
FIGS. 6 to 9 are block diagrams of third to sixth embodiments of this invention.

FIG. 6 shows an arrangement of the third system of this invention which is different from the first system in the arrangement of the modality.

Modalities 24a to 24c comprise modality data bases (MDBs) 71a to 71c coupled to IEs 50a to 50c. The MDBs 71a to 71c may be comprised of a rewritable TMD. MDBs 71a to 71c store image data acquired by IEs 50a to 50c, respectively. Modalities 24a to 24c comprise WSs 51a to 51c which read out image data temporally stored in MDBs 71a to 71c and display the read out image data.

In the system arranged as above, image data acquired by IEs 50a to 50c is stored in MDBs 71a to 71c. The image data stored in MDBs 71a to 71c is read out and displayed by WSs 51a to 51c. Doctors review the displayed images and input the finding results by using keyboards. Subsequently, the image data and review data are transferred to data bases 25a to 25c via network 22. As will be evident, even if image data is acquired in modalities 24a to 24c in parallel, the image data is not immediately transferred to network 22. Therefore, a collision of the image data on the network can be avoided.

Figure 7:
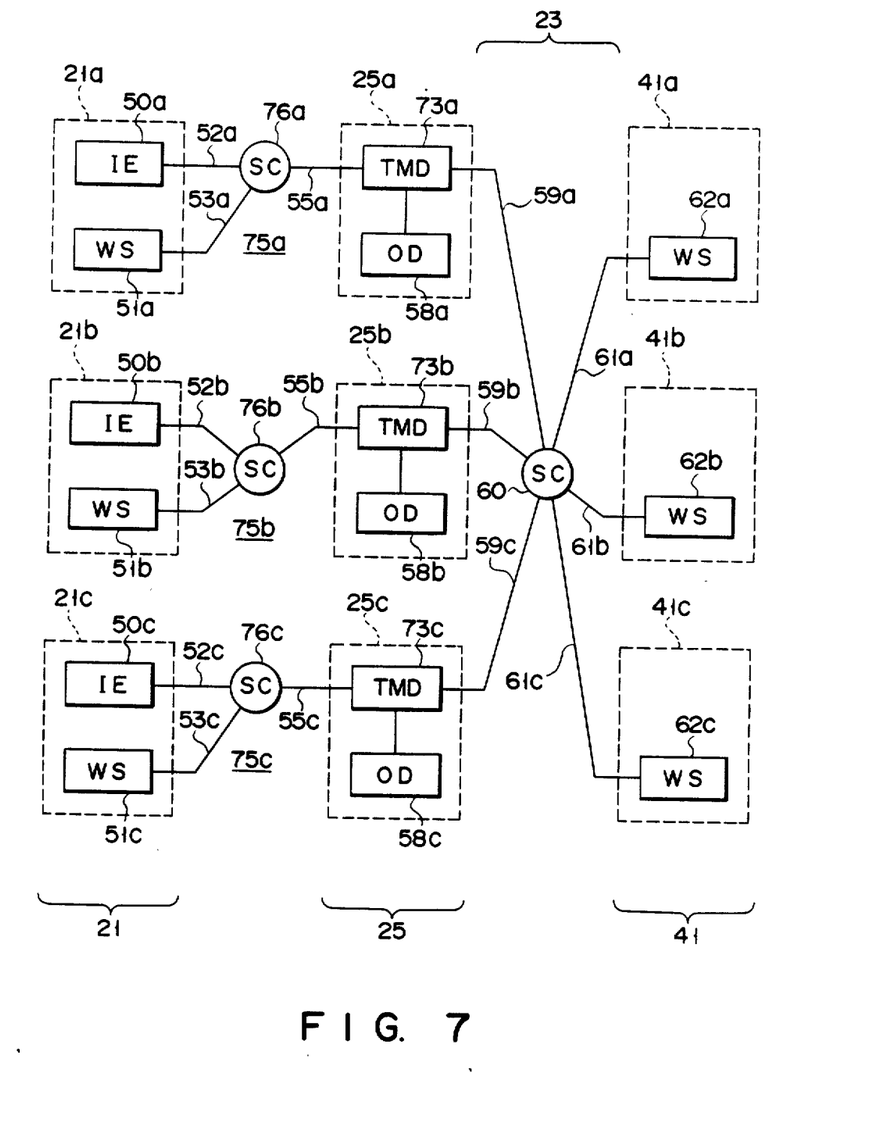

FIG. 7 shows an arrangement of the fourth system of this invention which is different from the first system in that modalities 21a to 21c are coupled to data bases 25a to 25c via independent networks 75a to 75c, respectively. Networks 75a to 75c have SCs 76a to 76c, respectively. In this system, data bases 25a to 25c store image data acquired by modalities 21a to 21c separately, by way of example, data bases 25a, 25b and 25c store X-ray images, X-ray CT images and ultrasound images, respectively. With such a system, when image data is transferred from IEs 50a to 50c to data bases 25a to 25c in parallel, a collision of the image data on the network can be avoided because the data transfer is performed through independent networks 75a to 75c.

Figure 8:
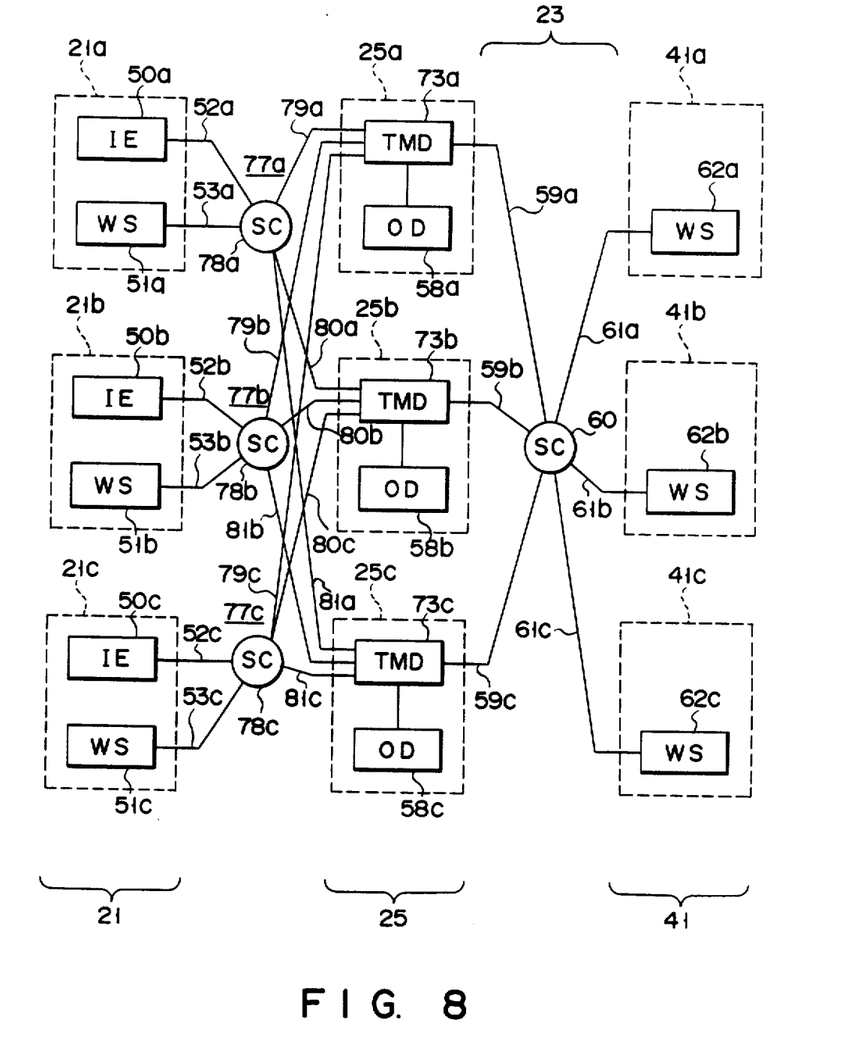

FIG. 8 shows an arrangement of the fifth system of this invention which is different from the first system in networks 77a to 77c. Image data acquired by IEs 50a to 50c is stored in TMDs 73a to 73c through lines 52a to 52c, SCs 78a to 78c, lines 79a to 79c, lines 80a to 80c and lines 81a to 81c in networks 77a to 77c.

When image data is stored in ODs 58a to 58c of data bases 25a to 25c, and the readout request of the image data is performed from WS 51a of modality 21a to data base 25, since image data is separately stored in data bases 25a to 25c, the image data is transferred from ODs 58a to 58c to TMDs 73a to 73c and then read out therefrom through networks 77a to 77c. At the same time, when the readout request of the image data is performed from WS 51b to data base 25, the necessary image data is read out by the similar operations to the above. Accordingly, even if image data is read out from WSs 51a to 51c of modalities 21a to 21c in parallel, the image data can smoothly be transferred.

The provision of the MDBs in IEs 50a to 50c of modalities 21a to 21c will allow the same advantages as above to be obtained. In this case, the image data acquired in modalities 21a to 21c is temporally stored in corresponding MDBs. The image data stored in the MDBs is read out by WSs 51a to 51c and then reviewed by doctors. After the review, the image data is transferred to data bases 25a to 25c via networks 77a to 77c.

According to such a system, even if image data is read out to modalities 21a to 21c in parallel, the image data can smoothly be transferred without any waiting time. As a result, the efficiency of image data transfer and throughput can be improved.

Figure 9:
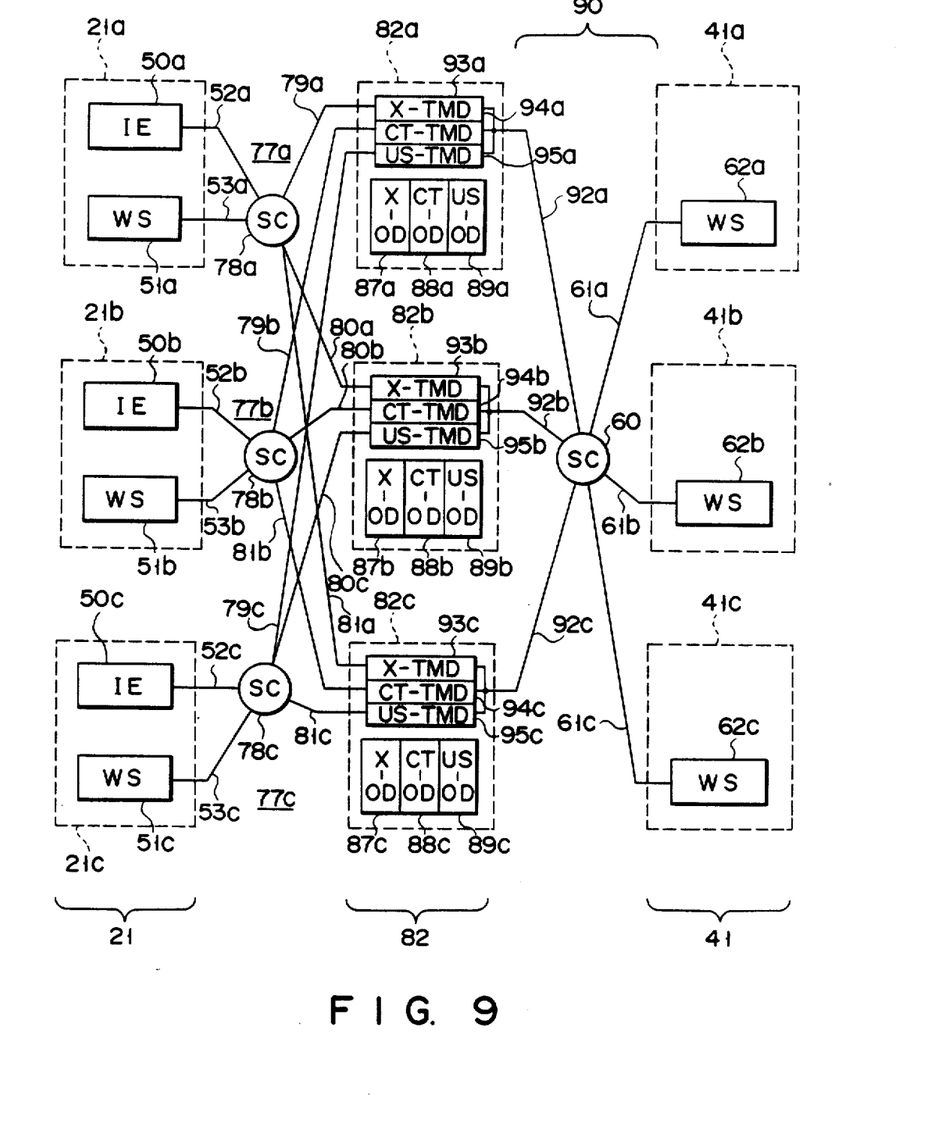
Figure 10:
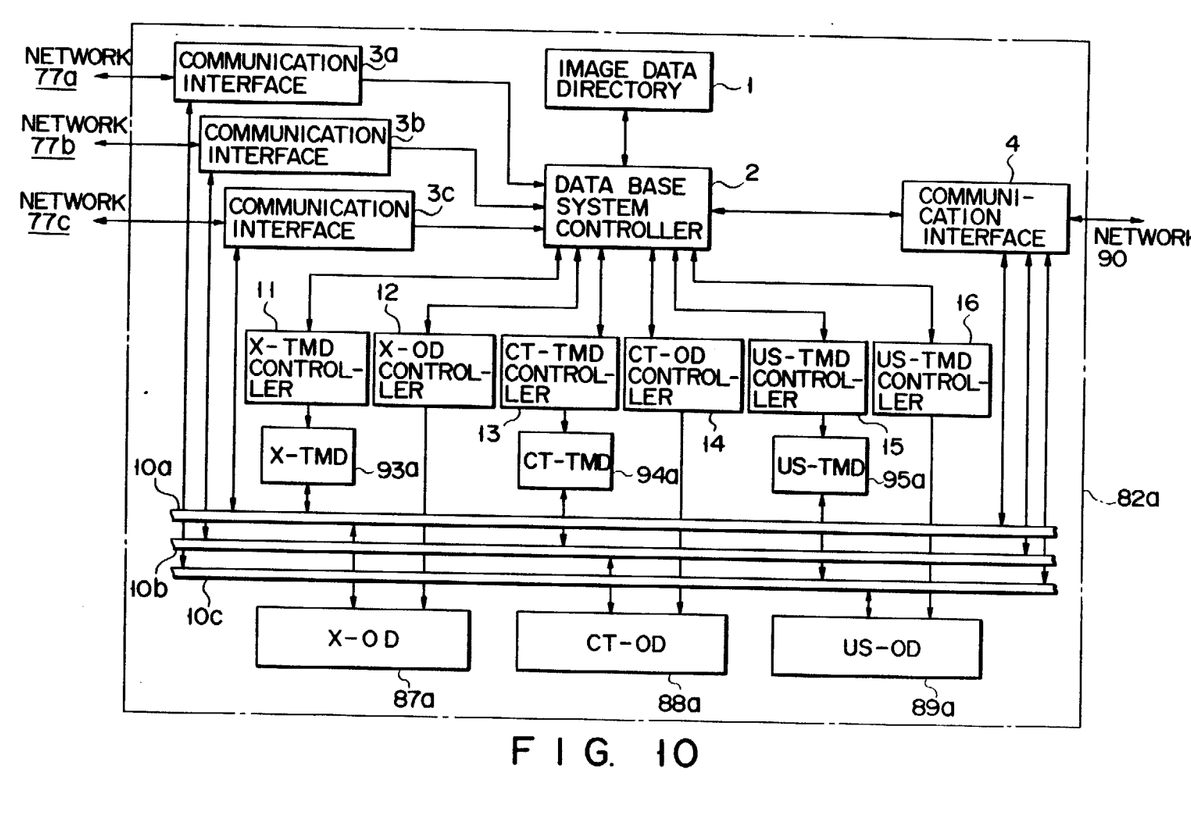
FIG. 10 is a block diagram of the data base shown in FIG. 9.

FIG. 9 shows an arrangement of the sixth system of this invention which differs from the fifth system in that data bases 82a to 82c of data base 82 each store image data acquired by each of modalities 21a to 21c. That is to say, as shown in FIG. 10, data base 82a, by way of example, comprises TMD 93a for storing X-ray image data, TMD 94a for storing X-ray CT image data, TMD 95a for storing ultrasound image data, OD 87a storing for X-ray image data, OD 88a for storing X-ray CT image data, and OD 89a for storing ultrasound image data. In addition, data base 82 includes controllers 11 to 16 for controlling them.

Consequently, data base 82a can store image data acquired by modalities 21a, 21b, 21c in independent TMDs 93a, 94a, 95a, respectively, via communication interfaces 3a to 3c and data bases 10a to 10c. Thus, even if image data is output from plural modalities to one data base in parallel, the image data can be transferred smoothly.

For example, when the readout request of image data is performed from WSs 51a and 51b to data base 82a in parallel, WS 51a accesses TMD 93a via network 77a, and, at the same time, WS 51b accesses TMD 94a via network 77b, thus resulting in no waiting time.

Figure 11:
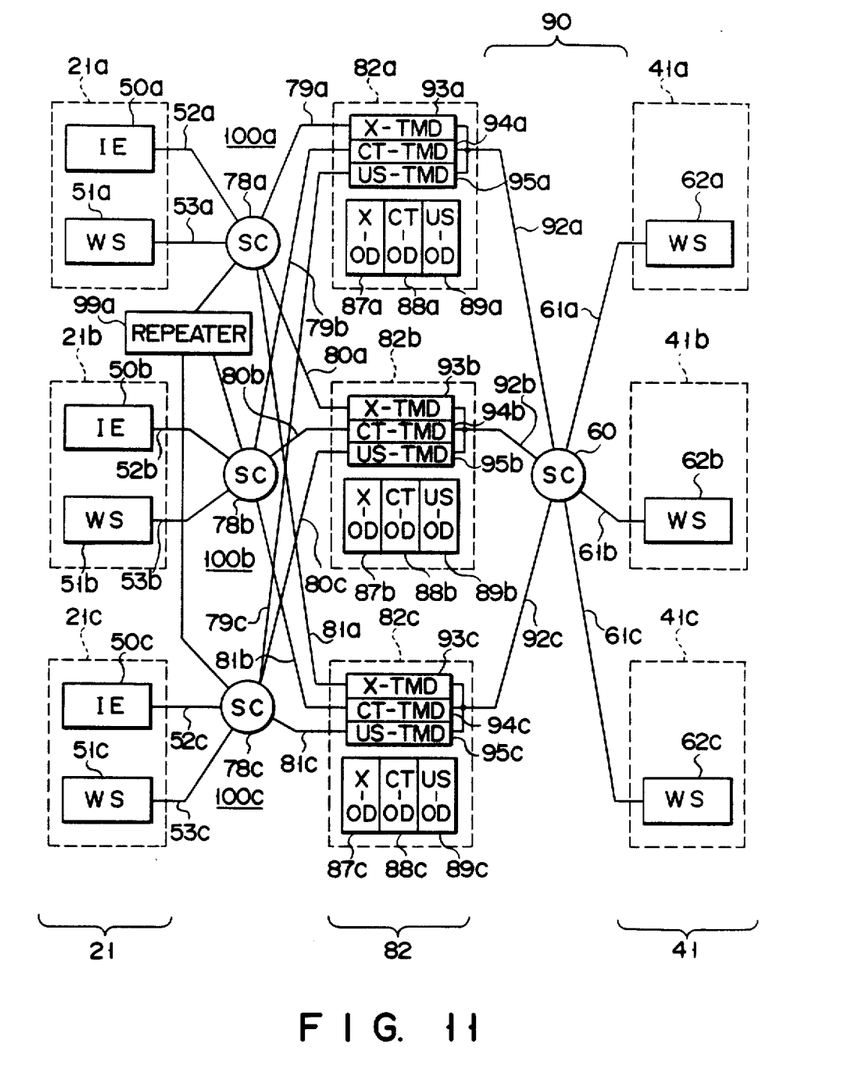
FIGS. 11 and 12 are block diagrams of seventh and eighth embodiments of this invention.

FIG. 11 shows an arrangement of the seventh system of this invention which differs from the sixth system in that networks 77a to 77c are connected through repeater 99a. Thus, data communication among networks 77a to 77c can be performed by using repeater 99a.

Repeater 99a may be formed of a star coupler and a light-amplifier (not shown).

Figure 12:
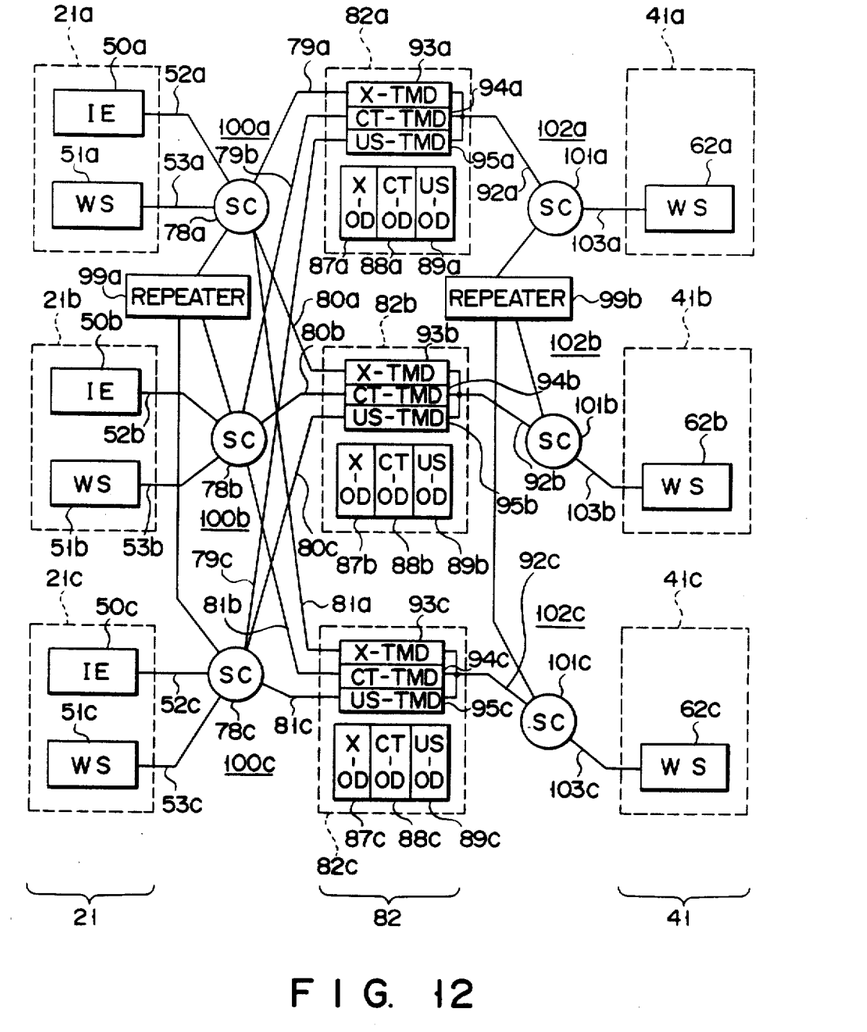

FIG. 12 shows an arrangement of the eighth system of this invention which is different from the seventh system in that consoles 41a to 41c have independent networks 102a to 102c connected thereto, and networks 102a to 102c are connected by a repeater 99b. That is, consoles 41a to 41c are coupled to data bases 82a to 82c via networks 102a to 102c having lines 103a to 103c, SCs 101a to 101c and lines 92a to 92c. communication can be performed among networks 102a to According to such a system arrangement, the data 102c. In this system, as an change of repeater 99b, each of SCs 101a to 101c may be coupled to data bases 82a to 82c by lines. This will provide the same advantage as that of the system shown in FIG. 12.

Although the preferred embodiments of this invention have been disclosed and described, it is apparent that other embodiments and modifications are possible.

What is claimed is:

1. A system for archiving and communicating medical image data, the system comprising:
   a plurality of modality means for producing medical image data;
   a plurality of storing means for acquiring the medical image data from the modality means and storing the medical image data, each of the plurality of storing means allocated to a predetermined medical group and having two independently accessible data bases;
   first network means for connecting the plurality of modality means respectively to one of the two data bases of each storing means;
   a plurality of work station means for selectively accessing the storing means to visually display the medical image data; and
   second network means for connecting the plurality of work station means respectively to the other of the two data bases of each storing means.

2. A system according to claim 1, wherein the medical image data includes at least one of X-ray image data, X-ray computed tomogram data, and ultrasound image data.

3. A system according to claim 2, wherein the modality means includes:
   imaging equipment means for obtaining the medical image data; and
   work station means for selectively accessing the storing means to visually display the medical image data.

4. A system according to claim 2, wherein the first network means includes a plurality of star coupler means for connecting the modality means to the storing means.

5. A system according to claim 2, wherein the second network means includes a plurality of star coupler means for connecting the storing means to the work station means.

6. A system for archiving and communicating medical image data, the system comprising:
   a plurality of modality means for producing medical image data;
   a plurality of storing means for acquiring the medical image data from the modality means and storing the medical image data;
   first network means for connecting the plurality of modality means respectively to the plurality of storing means, the first network means including a plurality of star coupler means for connecting the modality means to the plurality of storing means;
   a plurality of work station means for selectively accessing the storing means to visually display the medical image data; and
   second network means for connecting the plurality of work station means respectively to the plurality of storing means.

* * * * *